(12) United States Patent
Oonuki

(10) Patent No.: US 6,454,712 B1
(45) Date of Patent: Sep. 24, 2002

(54) ULTRASONIC DIAGNOSTIC APPARATUS AND ULTRASONIC IMAGE MEASURING APPARATUS

(75) Inventor: Masato Oonuki, Yaita (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/644,861

(22) Filed: Aug. 24, 2000

(30) Foreign Application Priority Data

Aug. 25, 1999 (JP) .......................................... 11-238768

(51) Int. Cl.[7] ................................................ A61B 8/00
(52) U.S. Cl. ........................ 600/437; 600/443; 600/459
(58) Field of Search ........................ 600/440, 441–447, 600/453–458, 459, 437, 407; 128/916

(56) References Cited

U.S. PATENT DOCUMENTS

| | | | | |
|---|---|---|---|---|
| 5,553,620 A | * | 9/1996 | Snider et al. ................ | 600/440 |
| 5,868,676 A | * | 2/1999 | McCabe et al. ............. | 600/454 |
| 5,919,138 A | * | 7/1999 | Ustuner ....................... | 600/443 |
| 6,001,061 A | * | 12/1999 | Ogishima et al. ........... | 600/440 |
| 6,149,594 A | * | 11/2000 | Rock et al. .................. | 600/437 |
| 6,273,857 B1 | * | 8/2001 | Aden ........................... | 600/437 |
| 6,306,089 B1 | * | 10/2001 | Coleman et al. ............ | 128/916 |

FOREIGN PATENT DOCUMENTS

JP  11-116385  4/1999

\* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

An ultrasonic diagnostic apparatus according to the present invention comprises an ultrasonic probe, a transmitting/receiving unit for transmitting and receiving an ultrasonic wave to and from a subject via an ultrasonic probe, an image generating unit for generating an ultrasonic image based on a signal obtained from the transmitted and received waves, an input means for selecting a desired measuring item and desired calculating item from a plurality of measuring items and calculating items, a measurement processor for performing measurement processing on the measuring item and measuring item necessary to calculation processing on the calculating item with the use of the ultrasonic image and performing calculation processing on the selected calculating item from the measured value of the measuring item necessary to the calculation processing on the selected calculating item, and a measurement managing processor for specifying a measuring item in a not-yet-measured state in the selected measuring item and measuring item necessary to the calculation processing on the selected calculating item and noticing the specified item.

21 Claims, 7 Drawing Sheets

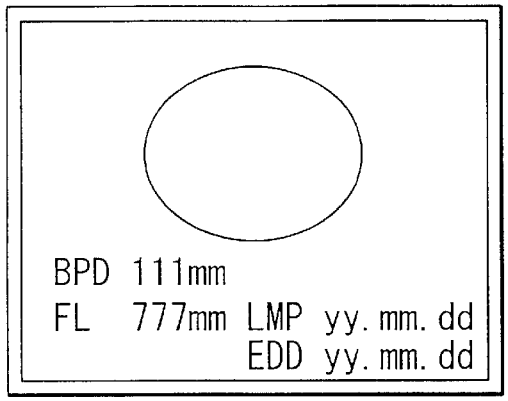

OBSTETRICS MESUREMENT

FIG. 1 PRIOR ART

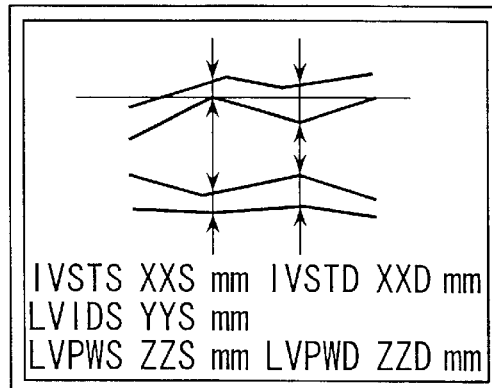

CARDIAC FUNCTION MEASUREMENT

FIG. 2 PRIOR ART

```
OB MEASUREMENT WORKSHEET
      1    2    3   AVG
CRL
BPD  111  222  333  222  mm
FT        555  666  555  mm
EL   777  888  999  888  mm
EFW 9999g
LMP yy.mm.dd
EDD yy.mm.dd
```

OBSTETRICS MESUREMENT

FIG. 3 PRIOR ART

```
LV MEASUREMENT WORKSHEET
      1    2    3   AVG
LV
IVSTS XXS  XSS  SXS  VVV  mm
LVIDS YYS  YSS  SYS  VVV  mm
LVPWS ZZS  ZSS  SZS  VVV  mm
IVSTD XXD  XDD  DXD  VVV  mm
IVSTD      YDD  DXD  VVV  mm
LVPWD ZZD  ZDD  DZD  VVV  mm
MV
```

CARDIAC FUNCTION MEASUREMENT

FIG. 4 PRIOR ART

| CATEGORY | CALCULATION ITEM | REQVIRED MEASUREMENT ITEM |
|---|---|---|
| OBSTETRICS | EFW | BPD   HC   AC   FL |
| | EDD | LMP |
| CARDIAC FUNCTION | EDV | LVIDD |
| | ESV | LVIDS |
| | SV | LVIDD   LVIDS |
| | CO | LVIDD   LVIDS   HR |
| | EF | LVIDD   LVIDS |
| | FS | LVIDD |
| MITRAL VALVE | CA/CE | CAAMP   CEAMP |
| AORTIC VALVE | LA/AO | LAD   AOD |
| BLOOD FLOW VOLUME | CSA | D |
| | FV | HR   D   ET   VEL |

FIG. 8

| CATEGORY \ ITEM | 1 | 2 | 3 | 4 | 5 | 6 |
|---|---|---|---|---|---|---|
| OBSTETRICS | BPD | OFD | HC | FTA | FL | AC |

FIG. 9

| CATEGORY \ ITEM | 1 | 2 | 3 | 4 | 5 | 6 |
|---|---|---|---|---|---|---|
| OBSTETRICS | ○ | × | × | × | ○ | △ |

FIG. 10

○ ··· MEASURED
△ ··· OUTSIDE ACCURATE RANGE
× ··· NOT-YET-MEASURED

```
NOT-YET-MEASURED
 : OFD, HC, FTA
OUTSIDE ACCURATE
 RANGE: min<AC<max)

BPD  XXX mm
FL   XXX mm   LMP yy.mm.dd
              EDD yy.mm.dd
```
OBSTETRICS MESUREMENT

FIG. 11

```
NOT-YET-MEASURED
 : LVIDD
OUTSIDE ACCURATE
 RANGE: min<IVISTD<max)

IVSTS   XXS mm   IVSTD  XXD mm
LVIDTS  YYS mm
LVPWS   ZZS mm   LVPWD  ZZD mm
```
CARDIAC FUNCTION
MEASUREMENT

FIG. 12

ULTRASONIC DIAGNOSTIC APPARATUS AND ULTRASONIC IMAGE MEASURING APPARATUS

CROSS-REFERENCE TO RELATED APPLICATIONS

This application is based upon and claims the benefit of priority from the prior Japanese Patent Application No. 11-238768, filed Aug. 25, 1999, the entire contents of which are incorporated herein by reference.

BACKGROUND OF THE INVENTION

The present invention relates to an ultrasonic diagnostic apparatus and ultrasonic image measuring apparatus having the function of measuring diagnostically useful information using various ultrasonic images of an M mode, B mode, Doppler mode, etc., and calculating index values from the calculated values.

Known are various medical applications of ultrasounds and their main stream is toward generating a tissue section image (B mode) of the soft tissue of a living body with the use of an ultrasonic pulse echo method and toward the so-called M mode in which a sequential morphological change of the heart and blood vessels, etc., can be observed in detail by arranging the tissue images on one line in parallel array along a time base. In comparison with the X-ray diagnostic apparatus, X-ray computed tomography apparatus (X-ray CT scanner), magnetic resonance imaging apparatus (MRI), nuclear medicine diagnostic apparatus such as the SPECT and PET, such ultrasonic image diagnosis is advantageous in that it is possible to observe, in realtime, the movement of the heart and fetus by a simpler operation of scanning the ultrasonic probe along a body surface or to obtain the spectrum and spatial broadening of the bloodstream by utilizing the Dopper effect. The ultrasonic image diagnosis has further advantages in terms of being much less adverse effect on the living body, allowing repeated use for check-up, and, in view of its being smaller in size, being movable along the bedside, and so on. For this reason, its application is to use in the heart, abdominal area, mammary gland, urological area, obstetric area, etc.

In many such ultrasonic diagnostic apparatus, however, an application program for the measurement of a structural dimension such as the distance from the B-mode image, area, volume, etc., and for the measurement of a temporal variation amount from the M mode image is attached as a standard or an optional function. The measurement result and calculation result can be displayed simply as a result as shown in FIGS. 1 and 2 and also can be edited freely on a worksheet as shown in FIGS. 3 and 4 and output collectively as a final result report.

In recent times, the measuring function has been specialized for use in the fetus and cardiovascular system, etc., and a vast number of items involved has to be measured. One example is as follows: For the measuring items involved in the obstetrics, there are, for example, AA: abdominal section area
OFD: fetal crown anterioposterior diameter
ATD: abdominal transverse diameters
LMP: last menstruation onset day
FL: femoral length
HA: fetal crown section area
ALD: abdomen anterioposterior diameter
KID: kidney length
THD: thorax diameter
CRL: fetal crown-rump length
AC: abdomen circumference length
FTA: trunk transverse area
BPD: biparietal diameter
HUM: humerus bone
FT: fetal leg length
SAC: gestational sac diameter
HC: fetal crown circumference length Further, as the calculating items using these, there are, for example, FEW: estimated fetus body weight (BPD+HC+AC+FL) and EDD: expected delivery date (LMP+280 days).

Further, even regarding the calculating methods of the measuring items, many authors insist on their own individual utility and significance and the selection of any specific calculating method are left to the user. For the EFW (assumed fetus body weight), there are 11 kinds of calculating methods currently available and the number are expected to be more and more increased in the future.

Under these situations, there is a tendency that the number of items to be selected is increased and it is not possible to fully grasp under which measuring items the selected calculation items have to be calculated. At a stage of opening the worksheet or report, therefore, the user often finds some items not filled under the measuring item. In this case, it is necessary to go back to the measuring mode involved and re-try the measurement processing with the not-yet-measured items added. This takes a cumbersome and time-consuming operation. For the measuring items, there is a given appropriate range and, outside this range, it is necessary to doubt a result of measurement. Even in this case, the user often finds it outside that range at a stage of opening the worksheet or report and, in the same way as above, it is necessary to go back to the measuring mode involved and re-try the measurement processing on that measuring item. This also takes a cumbersome and time-consuming operation.

BRIEF SUMMARY OF THE INVENTION

It is accordingly the object of the present invention to provide an ultrasonic diagnostic apparatus and ultrasonic image measuring apparatus which can beforehand prevent such a situation as to shift a current process to a worksheet- or a report sheet-editing operation with some measuring item left unmeasured or some measured item deviated from an appropriate value range.

An ultrasonic diagnostic apparatus comprising: an ultrasonic probe; a unit configured to transmit and receive an ultrasonic wave to and from a subject via the ultrasonic probe; a unit configured to generate an ultrasonic image based on signals obtained from the received ultrasonic waves; an input device configured to select a desired measuring items and desired calculating item from a plurality of measuring items and calculating items; a measuring unit configured to perform measurement processing on the selected measuring item with the use of the ultrasonic image and measuring item necessary to calculation processing on the selected calculating item and for performing calculation processing on the calculating item selected from the measured value of the measuring item necessary to the calculation processing on the selected calculation item; and a measurement managing unit configured to specify a measuring item in a not-yet-measured state from the selected measuring item and measuring item necessary to the calculation processing on the selected calculating item and noticing the specified measuring item.

According to the present invention, any measuring item in a not-yet-measured state, including not only the selected measuring item but also the measuring item necessary to calculation processing on the selected calculating item, is specified and so noticed and it is, therefore, possible to beforehand prevent such a situation as to go ahead with a current process with some measuring item left unmeasured.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 shows one form of conventional display screen for obstetrics measurement;

FIG. 2 shows one form of conventional display screen for measuring the cardiac function;

FIG. 3 shows one form of conventional worksheet display screen for an obstetrics measurement;

FIG. 4 shows one form of conventional worksheet display screen for measuring the cardiac function;

FIG. 8 shows a measuring item list necessary to calculating items stored in memory in FIG. 5;

FIG. 9 shows one form of measurement managing table prepared by a measurement managing processor in FIG. 5;

FIG. 10 shows a state in a given time of measuring items managed by the measurement managing processor (FIG. 5) with the use of the measurement managing table;

FIG. 11 shows one message display form of a not-yet-measured item and inappropriate item for obstetrics measurement by the measurement managing processor in FIG. 5;

FIG. 12 shows one form of message display of a not-yet-measured item and inappropriate item at a time of measuring a cardiac function by the measurement managing processor in FIG. 5;

DETAILED DESCRIPTION OF THE INVENTION

A preferred embodiment of the present invention will be explained below with reference to the accompanying drawing.

Figure 5:
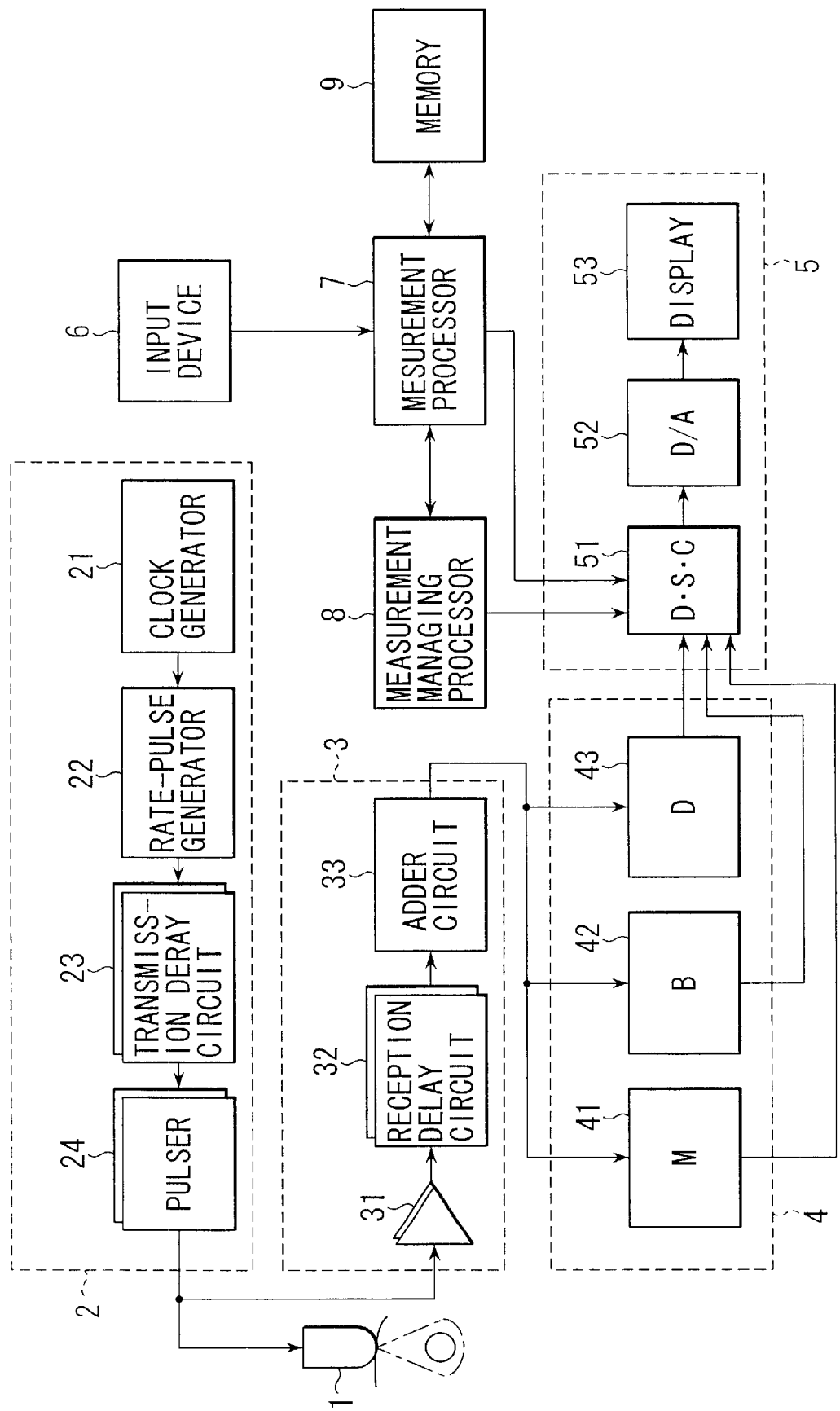
FIG. 5 is a schematic view showing an arrangement of an ultrasonic diagnostic apparatus according to an embodiment of the present invention.

FIG. 5 shows an arrangement of an ultrasonic diagnostic apparatus according to the present embodiment. In the neighborhood of the forward end of an ultrasonic probe 1, a plurality of oscillation elements are arranged with electrodes formed on both surfaces of a piezoelectric body such as a piezoelectric ceramics. Through the oscillation element, an electric signal (high frequency voltage) is converted to an ultrasonic wave and the ultrasonic wave is converted back to the electric signal. To the ultrasonic probe 1 are connected a transmitting unit 2 for applying the high frequency voltage to the oscillation element for generating the ultrasonic wave and a receiving unit 3 for receiving an echo back from a subject.

In the transmitting unit 2, a rate pulse is generated with a frequency of, for example, 6 kHz obtained by frequency-dividing a clock from a clock generator 21 into its small fraction past a rate pulse generator 22. As well known, this frequency is called a pulse repetition frequency PRF and an ultrasonic wave transmitting/receiving operation is repeated in synchronism with the pulse repetition frequency PRF. The rate pulse, after being delayed at a transmission delay circuit 23, is supplied to a pulser 24. The pulser 24 generates a high frequency voltage of a frequency f0 in synchronism with the rate pulse and applied it to the oscillation element. By doing so, from the probe 1 an ultrasonic beam is repeatedly transmitted toward the subject with a center frequency f0 and at a period corresponding to the reciprocal of the pulse repetition frequency PRF.

In the receiving unit 3, on the other hand, a feeble electric signal output from the oscillation element is first amplified with a preamplifier 31 and then delayed at a reception delay circuit 32 and added (phasing-added) at an adder 33. By doing so, a reception signal is generated with a specific direction component of the echo enhanced. This reception signal is sent to an ultrasonic image generation unit 4.

The ultrasonic image generation unit 4 has an M mode processor 41, B mode processor 42, and D mode processor 43. In the M mode processor 41, the reception signal is detected and the detected signal is logarithmically amplified at a logarithmic amplifier. By such processing, a tissue structure (acoustic impedance difference) on one beam line (acoustic scanning line) is represented by the amplitude variation. The amplified detected signal relating to any specific one ultrasonic scanning line is mapped, by a digital scan converter (D.S.C) 51 in a display unit 5, on an orthogonal coordinates system with a depth on the ordinate and the time on the abscissa and, by doing so, the so-called M mode image data is generated as data representing a time variation of the tissue structure on the one line.

In the B mode processor 42, the reception signal is detected and logarithmically amplified at a logarithmic amplifier and, by such processing, the tissue structure (acoustic impedance difference) on one beam line (ultrasonic scanning line) is displayed by the amplitude variation. In the B mode, the ultrasonic scanning line is moved by delaying control. The amplified detected signal is mapped, by the digital scanning converter (D.S.C) 51 in the display unit 5, on an orthogonal coordinates system with a depth as the ordinate and the direction as the abscissa and, by doing so, the so-called B mode image data is generated as data representing a section's tissue structure.

The D mode processor 43 has a Dopplar processing system for generating the so-called Doppler image representing a time variation of a frequency spectrum (velocity distribution) and a color Doppler processing system for generating the so-called color Doppler image representing a spatial distribution of the bloodstream in color. In the Dopplar processing system, the reception signal is orthogonally detected with a reference signal of a frequency f0 to extract a shift frequency component. And the detected signal is subjected to range gating and sample holding to cut a signal out of a sample volume and it is subjected by a fast Fourier transformation unit to frequency analysis to obtain spectrum information. This spectrum information is mapped, by the digital scan converter 51 in the display unit 5, on an orthogonal coordinates system with the frequency (velocity) as the ordinate and the time as the abscissa and, by doing so, the so-called color Dopper image data is generated as data representing a bloodstream in the section involved.

In the color Dopper processing system, the reception signal is orthogonally detected with a reference signal of a frequency f0 to take out a shift frequency component and a clutter at the cardiac wall, etc., is mainly removed with the use of a wall filter (MTI filter). A remaining bloodstream signal is subjected to autocorrelation processing and a result is calculated by a predetermined calculation formula to obtain bloodstream information (bloodstream velocity (average velocity), dispersion and power). This bloodstream information is mapped, by the digital scan converter 51 in the display unit 51, on an orthogonal coordinates system and, by doing so, the so-called color Dopper image data is generated as data representing a bloodstream distribution in the section.

The M mode image, B mode image, Doppler image, and color Dopper image (these are generally called as an ultrasonic image), generated by the digital scan converter 51 are supplied, in any combination, past a digital/analog converter (D/A) 52 to a display 53 for display.

This ultrasonic diagnostic apparatus gains a measuring function by having an input device 6, such as a mouse and keyboard, measurement processor 7, measurement managing processor 8 and memory 9. The measuring function includes not only the measurement processing for measuring a temporal shift from the M mode image, a structural dimension such as the distance, area, volume, etc., from the B mode image, and the bloodstream amount from the Doppler image, but also calculation processing for calculating index values (calculation value) of diagnostic benefit by their inherent calculation formulas with the use of results of measurement and processing for freely editing the results of measurement and results of calculation on the worksheet and finally outputting a research result as a report form.

There are the following items as the typical measuring and calculating items. As the category (classification), first an example for the obstetrics is given below:

AA: abdominal section area
OFD: fetal crown anterioposterior diameter
ATD: abdominal transverse diameters
LMP: last menstruation onset day
FL: femoral length
ALD: abdomen anterioposterior diameter
HA: fetal crown section area
KID: kidney length
CRL: fetal crown-rump length
THD: thorax diameter
AC: abdomen circumference length
FTA: trunk transverse area
HUM: humerus bone
BPD: biparietal diameter
SAC: gestational sac diameter
FT: fetal leg length
HC: fetal crown circumference length And there are following items, for example, as the calculation items using these:

EFW: estimated fetal body weight (calculation method BPD+HC+AC+FL)
EDD: expected deliver date (LMP+280 days)

As the measuring items relating to the cardiac function, there are

IVSTD: interventricular septum thickness at telediastolic phase
LVIDD: left ventricular minor axis diameter at telediastotic phase
LVPWD: left ventricular posterior wall thickness at telediastolic phase
IVSTS: interventricular septum thickness at end-systolic phase
LVIDS: left ventricular minor axis diameter at telesystolic phase
LVPWS: left ventricular posterior wall thickness at end-systolic phase
ET: ejection time
HR: heart rate (number of beats)

As the calculation items there are:

EDV: left ventricular volume at telediastolic phase
ESV: left ventricular volume at end-systolic phase
SV: stroke volume (EDV-ESV)
CO: cardiac output
EF: ejection fraction (SV/EDV)
FS: contraction rate ((LVIDD-LVIDS)/(LVIDD)

Further, as the measuring items relating to the mitral valve, there are:

CEAMP: E wave amplitude
DEAMP: DE wave amplitude
CAAMP: A wave amplitude
EPSS: E point.
DESLP: mitral valve opening speed
EFSLP: interventricular septum distance mitral valve retract speed As the measuring item, there is:

CA/CE: A wave B wave ratio (CAAMP/CEAMP), etc.

As the measuring items relating to the aortic valve, there are, for example,:

PVOTD: right ventricular outflow passage diameter
AOD: aorta diameter
AVD: aortic valve bore diameter
ET: ejection time
LAD: left atrium diameter As the calculation item, there is:

LA/AO: left atrium aorta ratio (LAD/AOD), etc.

As the measuring items relating to the bloodstream amount, there are, for example, D: diameter
HR: heart rate (number of beats)
ET: ejection time
VEL: bloodstream velocity As the calculating items, there are for example, CSA: section area $(\pi(D/2)^2)$
FV: bloodstream amount per minute (HR×CSA×$\int^{ET}$VELdt)

Figure 6:
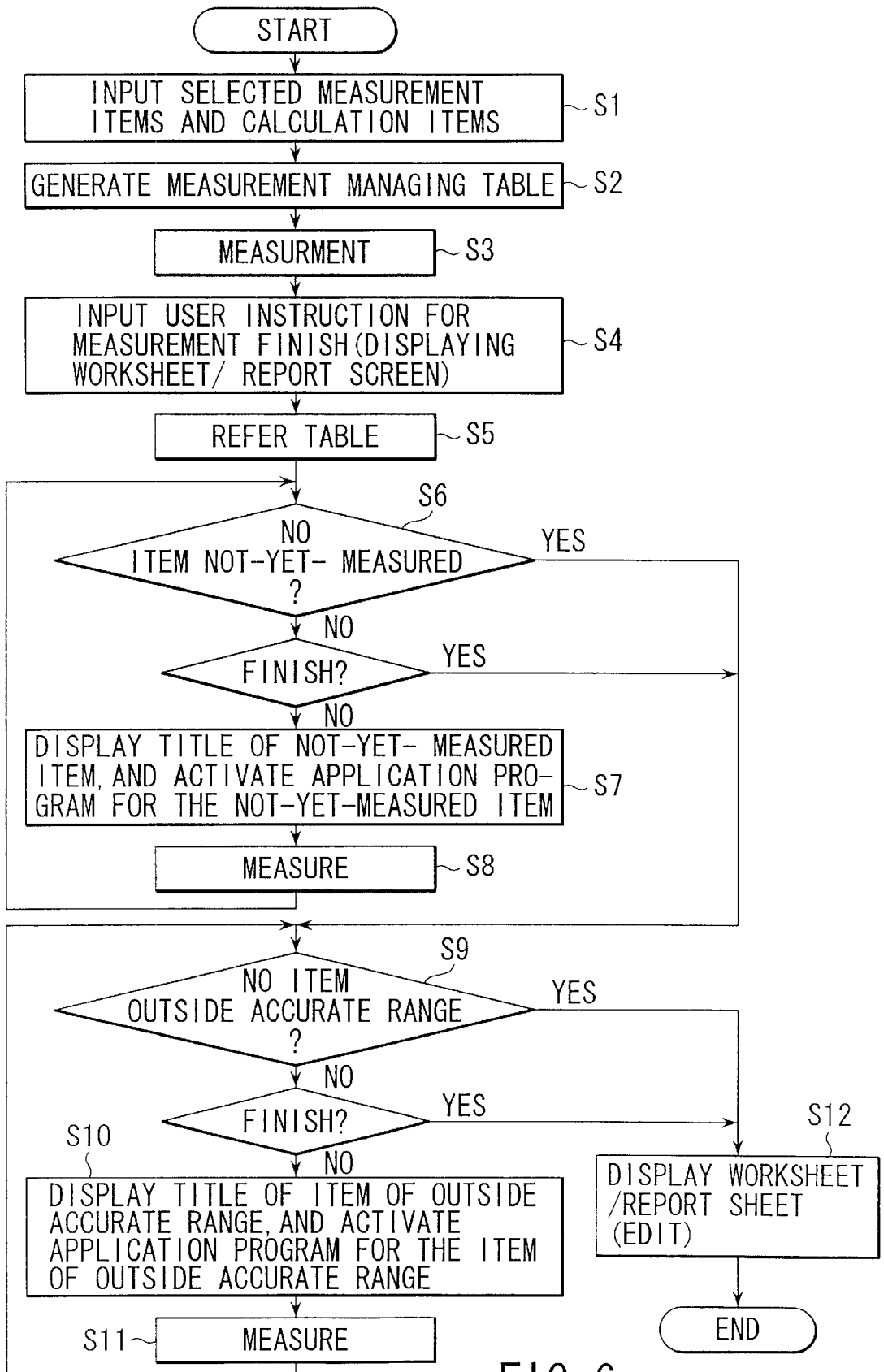
FIG. 6 is a flow chart showing a first measuring processing sequence of the present embodiment.
Figure 7:
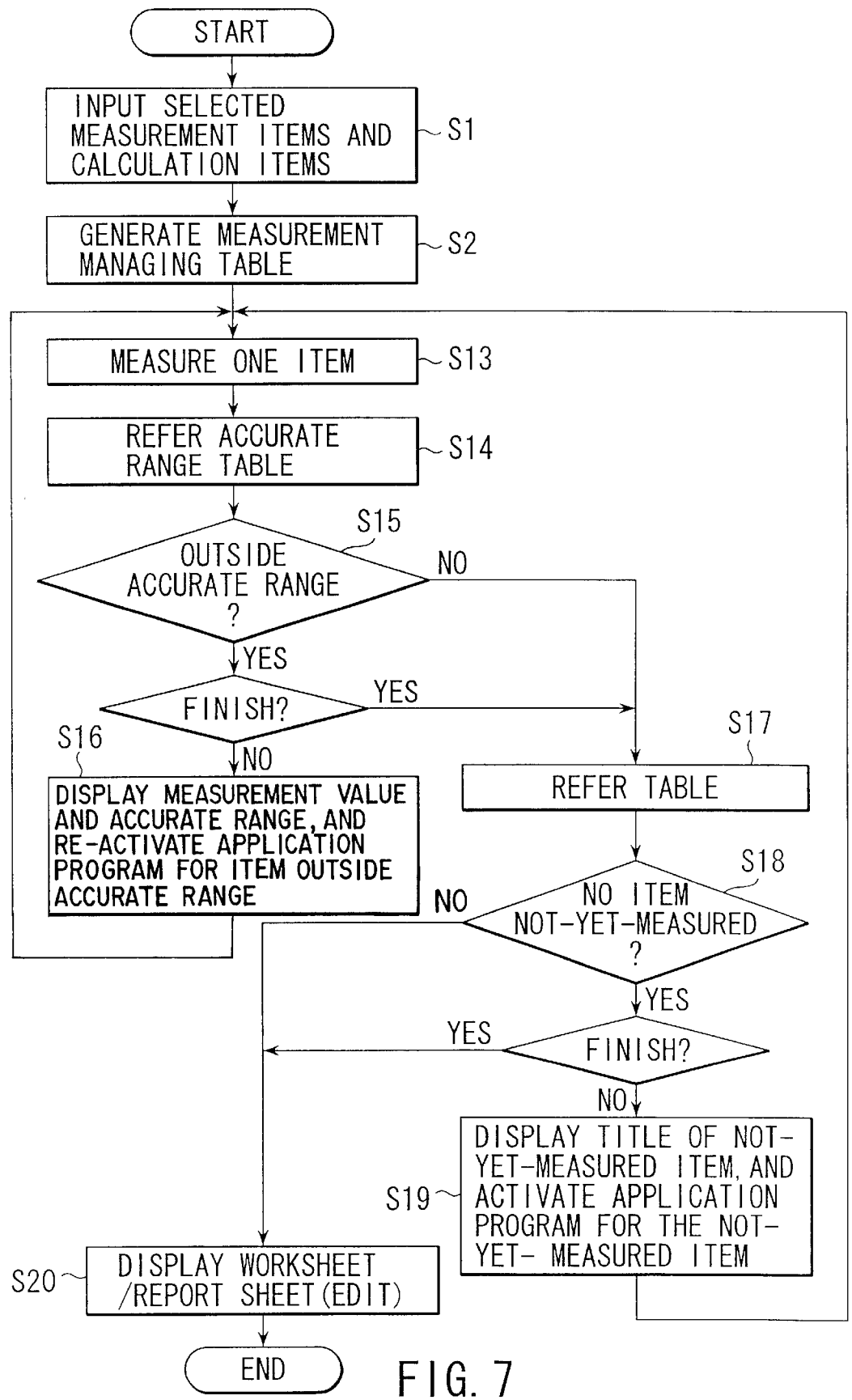
FIG. 7 is a flow chart showing a second measuring processing sequence of the present embodiment.

The measuring operation according to the present embodiment will be explained below together with a series of flow from the measuring operation to the worksheet/report edit operation. The present embodiment provides two kinds of measuring operation modes. The apparatus of the present embodiment may involve the use of any of two kinds of measuring operation modes or both the measuring operation modes in which case one of them may be selectively used in accordance with an instruction of the operator. FIG. 6 shows the first measuring operation mode and FIG. 7 the second measuring operation mode, as will be explained below.

FIRST MEASURING OPERATION MODE

First, when a measuring program installed in the memory 9 is started, then an item select screen is displayed, under this program, with executable measuring and calculating items set as lists. The operator designates at least one measuring item and at least one calculating item, as desired, with the use of the input device 6 (S1). In this case, it is possible to individually designate any desired measuring item and calculating item from among the lists and, when the category of measurement is designated, it is possible to designate, for this category, a typical item set, that is, a maker- or user-registered item set, at a time.

When the item selection is finished, a measurement managing table is prepared by the measurement managing processor 8 (S2). The measurement managing table is prepared as measuring item lists all necessary to the measurement as shown in FIG. 9, including not only the selected measuring item but also a measuring item necessary to calculation processing on those selected calculating items specifiable with the use of a correspondence table between the calculating item of FIG. 8 installed in the memory 9 and its required measuring item.

Then the measurement processing is performed, by the measurement processor 7, based on a point, curve, etc., designated by the operator or an ultrasonic image (S3). During the measurement operation, the measurement managing processor 8 timely attaches, as shown in FIG. 10, a "measured" or a "not-yet-measured" representing identifier (◯, x in FIG. 10) to a corresponding item in the measurement managing table. Further, the measurement managing processor 8 checks, while referring to the correspondence table between the item installed in the memory 9 and its appropriate range, whether or not the measured value and calculated value are within an appropriate range and, upon being outside the range, allows an identifier (Δ) to be attached to these values.

When the operator thinks that the measurement operation on the selected measuring item and measuring item necessary to the selected calculating item has been finished, he or she displays an edit screen of a worksheet and report and, in order to shift the current process to an edit operation on the worksheet and report, inputs the measurement finishing instruction through the input device 6 (S4).

When the measurement finished instruction is input, the measurement managing processor 8 refers to the measurement managing table before displaying the edit screen of the worksheet and report (S5). When even one "not-yet-measured" item is left on the measurement managing table (S6), then its "not-yet-measured" item or its list is message-displayed on the pop-up window as shown in FIGS. 11 and 12 and an application program for resuming the measurement operation on the "not-yet-measured" item is automatically started (S7).

Figure 13:
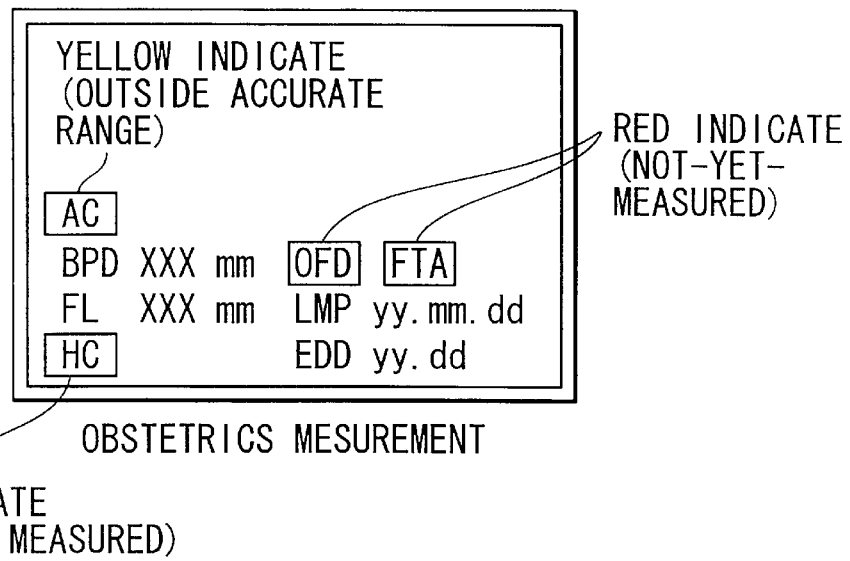
FIG. 13 is another display form of a not-yet-measured item and inappropriate item, as distinct from other items, at a time of the obstetrics measurement by the measurement managing processor in FIG. 5.
Figure 14:
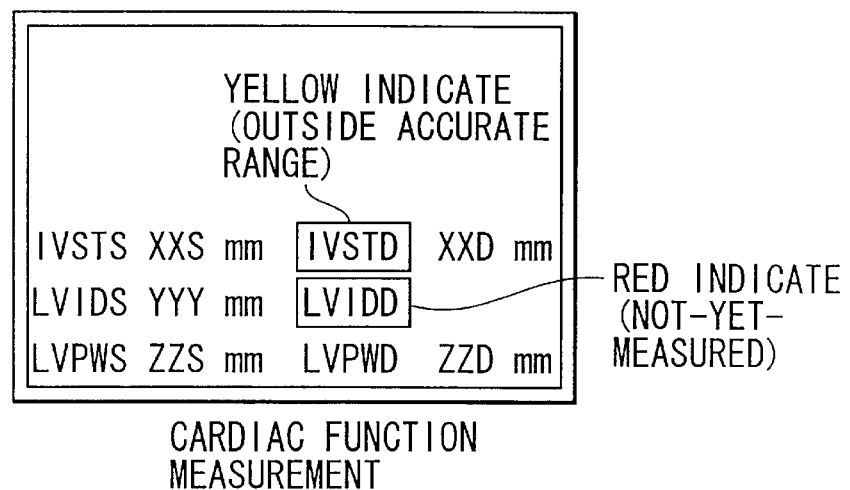
FIG. 14 is another display form of not-yet-measured item and inappropriate item, as distinct from other items, at a time of measuring the cardiac function by the measurement managing processor in FIG. 5.

It is to be noted that the display mode of the "not-yet-measured" item or its list is not restricted to the message display and may use any currently used various modes. As shown in FIGS. 13 and 14, for example, as the display mode, the title of the "not-yet-measured" item may be expressed in a different color from that of the "measured" item, or be underlined, or be flashed on and off, or its title name is generated as a tone.

Figure 15:
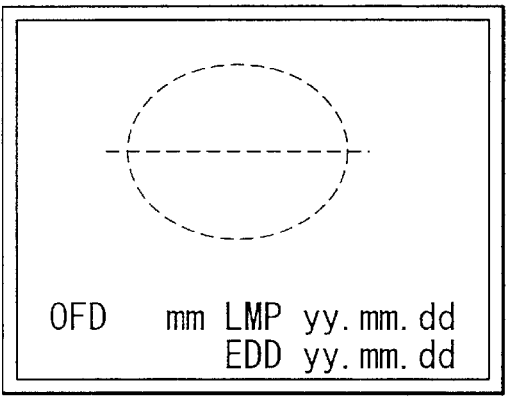
FIG. 15 shows one form of display screen at a time of re-trying a not-yet-measured item and inappropriate item involved at the obstetrics measurement by the measurement managing processor in FIG. 5.
Figure 16:
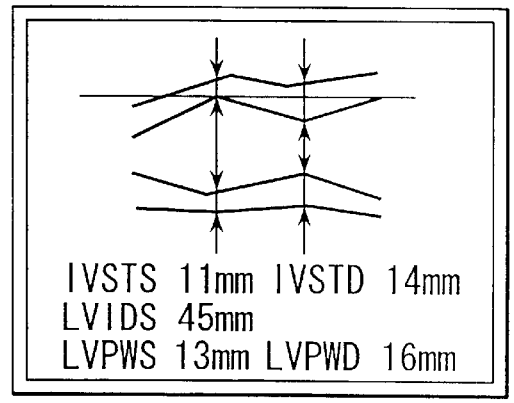
FIG. 16 shows one form of display screen at a time of re-trying a not-yet-measured item and inappropriate item involved at a time of measuring a cardiac function by the measurement managing processor in FIG. 5.

With the notice of the not-yet-measured item, as shown in FIGS. 15 and 16, a corresponding application program is automatically started and measurement operation is done in accordance therewith (S8).

Steps S6, S7 and S8 as set out above are repeated until there is no "not-yet-measured" item left. When it is decided that there remain no "not-yet-measured" item or items, the measurement managing processor 8 checks, while referring to an appropriate range table, whether or not a measured value involved is outside the appropriate range (S9). In this connection it is to be noted that the "appropriate" range is so set as to cover a very broad range outside which any measured value is completely deviated from a change resulting from a lesion, etc., as viewed from the clinical medicine. If the measured value is outside the appropriate range, it can be determined not as being an abnormal value resulting from the lesion, etc., in the evaluation of the clinical medicine but as being caused from other causes such as the measuring operation error.

The measurement managing processor 8 decides whether or not the measured values of all the measuring items fall within their appropriate range and, when it finds that there are no measured values deviated from the appropriate range, it supplies a control signal urging to start an edit operation of editing worksheet and report to the measurement processor (S12).

When, on the other hand, there is any one of the measuring items under which the measured value is deviated from the appropriate value, the measurement managing processor 8 message-displays the corresponding measuring item or its list on the pop-up window as shown in FIGS. 11 and 12 and an application program for resuming the measurement operation on the measuring item involved is started (S10).

The display mode of the inappropriate item or its list may be handled as in the case of the "not-yet-measured" item, that is, as shown in FIGS. 13 and 14, as the display mode, the title of the inappropriate item may be expressed in a different color from that of the appropriate item and the title of the inappropriate item may be underlined or flashed on and off or the title name may be produced as a tone.

With the notice of this inappropriate item, as shown in FIGS. 15 and 16, an application program of the not-measured item is automatically started and, in accordance therewith, the corresponding measuring operation is carried out (S11).

Steps S9, S10 and S11 as set out above are repeated until no inappropriate item is left. In this connection it is to be noted that even if there are no not-yet-measured item and inappropriate item left, the user can finish them at his or her own intention.

Since, in the first measuring operation mode, the not-yet-measured item and inappropriate item are automatically noticed before the current process is shifted to the edit operation of editing the worksheet and report, it is possible to avoid a very cumbersome and time-consuming operation from the edit operation of the worksheet and report back to the measuring operation. Further, the operator remembers his or her designated measuring item but it may often occur that he or she forgets the measuring item necessary to the designated calculating item. According to the present invention, such management including this is made and it is expected that the forgetting of the measuring item under this situation can be prevented. Even regarding the checking for an abnormal measurement, the operator cannot handle this unless he or she grasps the appropriate range and, even if he or she grasps the appropriate range, it is not practical to confirm the measured value and calculated value on an item-by-item basis and it may be possible that these are not detected on the side of the user. According to the present invention, on the other hand, such a situation is well managed on the apparatus side and can be prevented. As a result, any cumbersome operation, such as the restarting of the operation and re-checking can be prevented.

SECOND MEASURING OPERATION MODE

As in the same way as the first measuring operation mode, at least one measuring item and at least one measuring item are designated as desired (S1). And a measurement managing table is prepared by the measurement managing processor 8 (S2).

In accordance with an order on the measurement managing table, measurement processing is performed, by the measurement processor 7, on a respective measuring item on the basis of a point, curve, etc., designated by the operator on the ultrasonic image (S13).

When the measuring operation relating to one measuring item is finished, it follows that, before the shifting of the current process to the measuring operation on the next measuring item and before the shifting of the current process to an edit operation of editing the worksheet and report, the measurement managing processor 8 refers to the appropriate range table for the measured value (S14). When the measuring value is deviated from the appropriate range, the measurement managing processor 8 allows the measured value to be message-displayed, together with its appropriate range, on the pop-up window shown in FIGS. 11 and 12 and, in order to resume the measuring operation on the measured item involved, starts an application program automatically (S15).

With the notice of this inappropriate item, an application program is automatically started with respect to the inappropriate item as shown in FIGS. 15 and 16 and, in accordance therewith, the measuring operation is again performed (S16).

Steps S13, S14, S15 and S16 as set out above are repeated until the measured value is made to fall within an appropriate range.

At step S15, when the measured value falls within the appropriate range, the measurement managing processor 8 refers to the measurement managing table (S17) and, when even one "not-yet-measured" item is left (S18), the next measuring item is message-displayed on the pop-up window and an application program for starting the measuring operation on the above-mentioned next measuring item is automatically started (S19). And control goes back to step S13 and the measuring operation is performed on the above-mentioned next measuring item.

In this way, the processing at steps S13 to S19 is performed on all the measuring items and, when all the measuring items are found as being not inappropriate items and when there is not-yet-measured item left, that is, when a decision "NO" is made at step S18, then the current process is shifted to the edit operation of editing a worksheet and report (S20).

In this connection it is to be noted that, even when there are any not-yet-measured item and inappropriate item left, the user can finish them at his or her own intention.

Since, in this way, the second measuring operation mode is such that since, before a shift to the edit operation for editing the worksheet and report and at each finish of the measurement operation on the respective measuring item, it is automatically decided whether or not the measured value is within the appropriate range and whether or not there is no not-yet-measured item left, any such cumbersome and time-consuming situation as to go back to the corresponding measurement operation either after the measurement operation on other measuring item or still more from the edit operation for editing the worksheet or report can be avoided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
   an ultrasonic probe;
   a unit configured to transmit and receive an ultrasonic wave to and from a subject via the ultrasonic probe;
   a unit configured to generate an ultrasonic image based on signals obtained from the received ultrasonic waves;
   an input device configured to select a desired measuring item and a desired calculating item from a plurality of measuring items and calculating items;
   a measuring unit configured to perform measurement processing on the selected measuring item with the use of the ultrasonic image and a measuring item necessary to perform calculation processing on the selected calculating item, and to perform calculation processing on the selected calculating item; and
   a measurement managing unit configured to notice and specify a missed measuring item from the selected measuring item and the measuring item necessary to the calculation processing on the selected calculating item.

2. An ultrasonic diagnostic apparatus according to claim 1, wherein, after a finish of all measurement operations on the selected measuring item and the measuring item necessary to the calculation processing on the selected calculating item, but before a shift to an edit operation on a worksheet and/or report sheet, the measurement managing unit notices and specifies the missed measuring item.

3. An ultrasonic diagnostic apparatus according to claim 1, wherein, after a finish of respective measurement operation on the selected measuring item and the measuring item necessary to the calculation processing on the selected calculating item, but before a shift to a next measuring operation on another measuring item, the measurement managing unit notices and specifies the missed measuring item.

4. An ultrasonic diagnostic apparatus according to claim 1, wherein the measurement managing unit has a function of automatically starting a program configured to perform a measurement operation on the missed measuring item.

5. An ultrasonic diagnostic apparatus according to claim 1,
wherein the missed measuring item is displayed so a title thereof is expressed in a different color from a measured measuring item or is noticed by a tone.

6. An ultrasonic diagnostic apparatus according to claim 1, wherein the measurement management unit prepares a measurement managing table for managing the selected measuring item and the missed measuring item from the selected measuring item and the measuring item necessary to the calculation processing on the selected calculating item.

7. An ultrasonic diagnostic apparatus comprising:
an ultrasonic probe;
a unit configured to transmit and receive an ultrasonic wave to and from a subject via the ultrasonic probe;
a unit configured to generate an ultrasonic image based on a signal obtained by the transmitted and received signals;
an input unit configured to select a desired measuring item and a desired calculating item from a plurality of measuring items and calculating items;
a measuring unit configured to perform measurement processing on the selected measuring item with the use of the ultrasonic image, and to perform calculation processing on the selected calculating item; and
a measurement managing unit configured to notice when a result of the measurement processing on the selected measuring item and the selected calculating item is deviated from an inherent appropriate range.

8. An ultrasonic diagnostic apparatus according to claim 7, wherein, after a finish of all the measurement operations on the selected measuring item and a measuring item necessary to the calculation processing on the selected calculating item, but before a shift to an edit operation of a worksheet and/or report sheet, the measuring management unit notices and specifies a measured measuring item deviated from the appropriate range.

9. An ultrasonic diagnostic apparatus according to claim 7, wherein, after a finish of respective measuring operations on the selected measuring item and the measuring item necessary to the calculation processing on the calculating item, but before a shift to a measuring operation on a next measuring item, the measurement managing unit decides whether or not a measured value falls within the appropriate range and notices a result.

10. An ultrasonic diagnostic apparatus according to claim 7, wherein the measurement managing unit has a function of automatically starting a program for performing the measurement operation on a measuring item is deviated from the appropriate range.

11. An ultrasonic diagnostic apparatus according to claim 7, wherein the measuring item deviated from the appropriate range is displayed so a title thereof is made different from the measuring item falling within the appropriate range by a message display, and is noticed by a tone.

12. An ultrasonic diagnostic apparatus comprising:
an ultrasonic probe;
a unit configured to transmit and receive an ultrasonic wave to and from a subject via the ultrasonic probe;
a unit configured to generate an ultrasonic image based on a signal obtained from the transmitted and received waves;
an input device configured to select a desired measuring item from a plurality of measuring items; and
a measuring unit configured to perform measurement processing on the selected measured item with the use of the ultrasonic image,
wherein after a finish of all measuring operations on the selected measuring item, but before a shift to an edit operation of a worksheet and/or report sheet, a measurement managing unit notices and specifies a missed measuring item.

13. An ultrasonic diagnostic apparatus comprising:
an ultrasonic probe;
a unit configured to transmit and receive an ultrasonic wave to and from a subject via the ultrasonic probe;
a unit configured to generate an ultrasonic image based on a signal obtained from the transmitted and received waves;
an input device configured to select a desired measuring item from a plurality of measuring items; and
a measuring unit configured to perform processing on the selected measuring item with the use of the ultrasonic image,
wherein after respective measuring operations on the selected measuring item but before a shift to a next measurement operation on another selected measuring item, a measurement managing unit notices and specifies a missed measuring item.

14. An ultrasonic diagnostic apparatus comprising:
an ultrasonic probe;
a unit configured to transmit and receive an ultrasonic wave to and from a subject via the ultrasonic probe;
a unit configured to generate an ultrasonic image based on a signal obtained from the transmitted and received waves;
an input device configured to select a desired measuring item from a plurality of measuring items; and
a measuring unit configured to perform measurement processing on the selected measuring item with the use of the ultrasonic image,
wherein after a finish of all measuring operations on the selected measuring item, but before a shift to an edit operation of a worksheet and/or report sheet, a measurement managing unit notices and specifies a measuring item whose measured value is outside an appropriate range.

15. An ultrasonic diagnostic apparatus comprising:
an ultrasonic probe;
a unit configured to transmit and receive an ultrasonic wave to and from a subject via the ultrasonic probe;
a unit configured to generate an ultrasonic image based on a signal obtained from the transmitted and received waves;
an input device configured to select a desired measuring item from a plurality of measuring items;

a measuring unit configured to perform measurement processing on the selected measuring item with the use of the ultrasonic image; and a measurement managing unit configured to decide, after a finish of a respective measurement operation on the selected measuring item but before a shift to a next measurement operation on the measuring item, whether or not a measured value is deviated from an appropriate range and to notice a result.

16. An ultrasonic image measuring apparatus, comprising:

an input device configured to select a desired measuring item from a plurality of measuring items;

a measuring unit configured to perform measurement processing on the selected measuring item with the use of an ultrasonic image; and a measurement managing unit configured to notice and specify a missed measuring item from the selected measuring item.

17. An ultrasonic image measuring apparatus comprising:

input means for selecting a desired measuring item from a plurality of measuring items;

a measuring unit configured to perform measurement processing on the selected measuring item with the use of an ultrasonic image; and a measurement managing unit configured to notice when the selected measuring item has a measured value deviated from an inherent appropriate range.

18. A measuring method for an ultrasonic diagnostic apparatus comprising the steps of:

transmitting and receiving an ultrasonic wave to and from a subject and finding a corresponding ultrasonic image;

finding a value of a measuring item on a basis of the ultrasonic image;

checking whether or not a measurement operation on a measuring item necessary to a calculation operation on a calculating item is finished; and noticing a missed measuring item, wherein after a finish of the measurement operation on the measuring item necessary to the calculation operation of the calculating item, a value of the calculating item on the basis of the measuring item is found.

19. A measuring method for an ultrasonic diagnostic apparatus comprising the steps of:

transmitting and receiving an ultrasonic wave to and from a subject and finding a corresponding ultrasonic image;

finding a value of a measuring item on a basis of the ultrasonic image;

checking whether or not a value of a measuring item necessary to a calculation operation on a calculating item is an appropriate value; and noticing a measuring item whose measured value is not appropriate, wherein after all measuring items necessary to the calculation operation on the calculation item are appropriate, a value of the calculating item based on the value of the measuring item is found.

20. A measuring method for an ultrasonic diagnostic apparatus, comprising the steps of:

transmitting and receiving an ultrasonic wave to and from a subject and finding a corresponding ultrasonic image;

selecting, from a plurality of measuring items, a plurality of items whose values are to be found;

finding a value of a selected item based on the ultrasonic image;

checking whether or not a measurement operation on the selected item is finished; and noticing a missed measuring item.

21. A measuring method for an ultrasonic diagnostic apparatus comprising the steps of:

transmitting and receiving an ultrasonic wave to and from a subject and finding an ultrasonic image;

selecting, from a plurality of measuring items, a plurality of items whose values are to be found;

finding a value of a selected item based on the ultrasonic image;

checking whether or not the value of the selected item is an appropriate value; and noticing the selected item if the value is not appropriate.

* * * * *

UNITED STATES PATENT AND TRADEMARK OFFICE
CERTIFICATE OF CORRECTION

PATENT NO.     : 6,454,712 B1
DATED          : September 24, 2002
INVENTOR(S)    : Onuki It is certified that error appears in the above-identified patent and that said Letters Patent is hereby corrected as shown below:

<u>Title page,</u>
Items [12] and [75], should read:

-- [12] United States Patent
        Onuki --

-- [75] Inventor: Masato Onuki, Yaita (JP) --

Signed and Sealed this

Eighteenth Day of February, 2003

JAMES E. ROGAN
*Director of the United States Patent and Trademark Office*